(12) United States Patent
Reinhold

(10) Patent No.: US 7,343,203 B2
(45) Date of Patent: Mar. 11, 2008

(54) APPARATUS FOR ELECTROTHERAPY

(75) Inventor: Walter Reinhold, Schnaittach (DE)

(73) Assignee: Physiomed Elektromedizin AG, Schnaittach/Laipersdorf (DE)

( * ) Notice: Subject to any disclaimer, the term of this patent is extended or adjusted under 35 U.S.C. 154(b) by 361 days.

(21) Appl. No.: 10/986,884

(22) Filed: Nov. 15, 2004

(65) Prior Publication Data

US 2005/0107848 A1  May 19, 2005

(30) Foreign Application Priority Data

Nov. 13, 2003 (DE) ................ 103 53 000

(51) Int. Cl.
*A61N 1/32* (2006.01)
(52) U.S. Cl. .................. 607/63; 607/2; 607/46; 607/145
(58) Field of Classification Search ........... None
See application file for complete search history.

(56) References Cited

U.S. PATENT DOCUMENTS

| 3,640,284 | A | * | 2/1972 | De Langis | 607/71 |
| 4,033,356 | A | * | 7/1977 | Hara | 607/152 |
| 4,541,432 | A | * | 9/1985 | Molina-Negro et al. | 607/46 |
| 4,976,263 | A | * | 12/1990 | Seidl et al. | 607/63 |
| 5,186,171 | A | * | 2/1993 | Kuhry | 607/68 |
| 5,476,481 | A | * | 12/1995 | Schondorf | 607/2 |
| 5,817,138 | A | * | 10/1998 | Suzuki | 607/67 |
| 6,096,063 | A | * | 8/2000 | Lopin et al. | 607/8 |
| 6,236,890 | B1 | * | 5/2001 | Oldham | 607/68 |
| 6,676,686 | B2 | * | 1/2004 | Naganuma | 607/1 |
| 6,740,079 | B1 | * | 5/2004 | Eggers et al. | 606/34 |
| 2001/0044640 | A1 | * | 11/2001 | Akiyama et al. | 607/2 |

FOREIGN PATENT DOCUMENTS

| DE | 8630690 U1 | 2/1987 |
| DE | 3716816 C2 | 2/1988 |
| DE | 3734036 A1 | 2/1988 |
| DE | 3318874 C2 | 8/1990 |
| WO | WO 93/09843 A1 | 5/1993 |

\* cited by examiner

*Primary Examiner*—Kristen D. Mullen
*Assistant Examiner*—Eugene T Wu
(74) *Attorney, Agent, or Firm*—Browdy and Neimark, PLLC

(57) ABSTRACT

In an apparatus for electrotherapy, comprising a circuit arrangement with a terminal for generation of a sequence of voltage pulses and two electrodes for application of these voltage pulses to a part of the body that is to be treated; one of the two electrodes having a surface of comparatively high transition resistance and the other electrode having comparatively low transition resistance towards human skin; the electrode with the surface of high transition resistance being movable over the treated part of the body and the surface being a plastic film; with sequences of pulses of voltages from 1 to 600 V being generated and a current in a microampere range being produced in the tissue; it is provided that the rapid discharge circuit comprises several thyristors which are triggered by optocouplers.

12 Claims, 2 Drawing Sheets

APPARATUS FOR ELECTROTHERAPY

BACKGROUND OF THE INVENTION

1. Field of the Invention

The invention relates to an apparatus for electrotherapy, comprising in particular a circuit arrangement with a terminal for generation of a sequence of voltage pulses and two electrodes for application of these voltage pulses to a part of the body that is to be treated; one of the two electrodes having a surface of comparatively high transition resistance and the other electrode having comparatively low transition resistance towards the human skin; the electrode with the surface of high transition resistance being movable over the part of the body that is to be treated and the surface being a plastic film; with sequences of pulses of voltages from 1 to 600 V being generated and a current in a microampere range being produced in the tissue.

2. Background Art

An apparatus of the generic type is known from U.S. Pat. No. 4,976,263.

An apparatus of the generic type helps accomplish a flow in the human tissue of currents of extremely low amperage i.e., in the microampere range. This is due to the high transition resistance of the at least one electrode, with a current limiter precluding any risk for a treated person occasioned by the comparatively high voltage used, even in cases that deviate from the norm, for example surrounding high moisture content.

The pulse sequences applied to a treated part of the body modulate the physiotherapeutic effect on the tissue periodically corresponding to the excitation frequency, this having an extremely efficient decongestive effect on lymph, overacidified muscles, bruises or the like by autonomous regeneration of the connective tissue, i.e. any accumulation of concentrations in the tissue is intercepted.

The efficacy of physiotherapeutic devices of the generic type is based on endogenous modulation. A treated person as well as a therapist will only observe body pulsation or vibration. Moreover, this kind of excitation can make use of frequencies which are hard to be put into practice by purely mechanical excitation. Precise control of the dynamics of the vibratory motion is possible by excitation of corresponding pulse patterns.

The effect which the efficacy of such a device depends on is, among other things, based on periodical modification of the frictional force between a therapist's glove, or the metal electrode he moves, and the treated tissue by reason of a phenomenon similar to the Johnson-Raabeck effect. Semiconductor-type behaviour of one of the electrodes, namely the moved electrode, is of decisive importance for the occurrence of this effect.

The pulsating electric field between a therapist's hand and a patient's body leads to pulsating electrostatic attraction and thus to pulsating frictional force, this ultimately leading to even sensible pulsating tissue deformation.

SUMMARY OF THE INVENTION

It is an object of the invention to improve the effect, known per se, of a device of the generic type that has proved extraordinarily successful.

This object is attained by a rapid-discharge circuit being provided.

It has been known per se, in devices of the generic type, to provide rapid-discharge circuits which are necessary because of the lack of self-discharge of the electrode of high transition resistance. According to the invention, a self-discharge circuit is embodied for inclusion of several thyristors that are triggered by optocouplers. In this way it is possible to produce positive and negative pulses in succession which counteract any ensuing polarization of the film; in particular it is possible in this way to produce higher voltage frequency, which will clearly increase treatment efficiency.

In stimulation-current devices, such a circuit can be used advantageously for generating of bi-phase pulses, which are conventionally produced by the aid of relays.

In keeping with another embodiment of the invention, it is provided that a basic frequency of 5 to 250 Hz, for example in an order of magnitude of 100 Hz is superimposed by a frequency of 1 to 30 Hz, for example in an order of magnitude of 1 to 10 Hz.

It has been known per se, in apparatuses of the generic type, to implement pulse frequency modulation, with the prior art apparatus being based on a basic frequency of 30 Hz.

As opposed to this, the invention has found that especially high efficiency can be obtained by the superimposed frequencies differing comparatively strongly, for example by an order of magnitude of a factor of 100. Consequently, it is possible to use a comparatively high frequency of for instance 120 Hz on the one hand and a comparatively low frequency of 1 Hz on the other.

Corresponding to lymph resonant vibration, the higher basic frequency occasions lymph-transported load such as proteins, by whirl-up thereof, to become transportable or to be rendered transportable again, whereas the lower frequency, as so-called burst frequency, stimulates lymphatic motoricity and thus discharge via the lymphatic system.

Continuous or randomised frequency bands are used preferably, ensuring stimulation of various tissue and nerve structures.

A foot-actuated switch advantageously enables switchover of the working parameters, for example frequencies, even in cases when a therapist needs both his hands, working for example with two glove electrodes, or in case of self-treatment.

The apparatus according to the invention also comprises an electrode arrangement, on the one hand including the electrode of comparatively high transition resistance that is passed over a patient's skin, and on the other hand the metal electrode of low transition resistance which can either be covered mechanically or switched off electrically, selectively acting only in case of self-treatment and when the metal electrode, while held or moved, is touched by a respective person's hand.

The electrode arrangement can comprise a handle into which releasably to insert the high-resistance electrode.

In this regard, the high-resistance electrode can advantageously be provided with a spring-basket-type plug for insertion into a corresponding sleeve of the handle.

The electrode plate of the high-resistance electrode is covered by electrically conductive foam material, which is covered by preferably vinyl-based plastic film; in accordance with the invention, a hydrogel disk is inserted between the foam material and the plastic film, ensuring excellent implementation of the desired effect.

Details of the invention will become apparent from the ensuing description of a preferred embodiment, taken in conjunction with the drawing.

DESCRIPTION OF A PREFERRED EMBODIMENT

Figure 1:
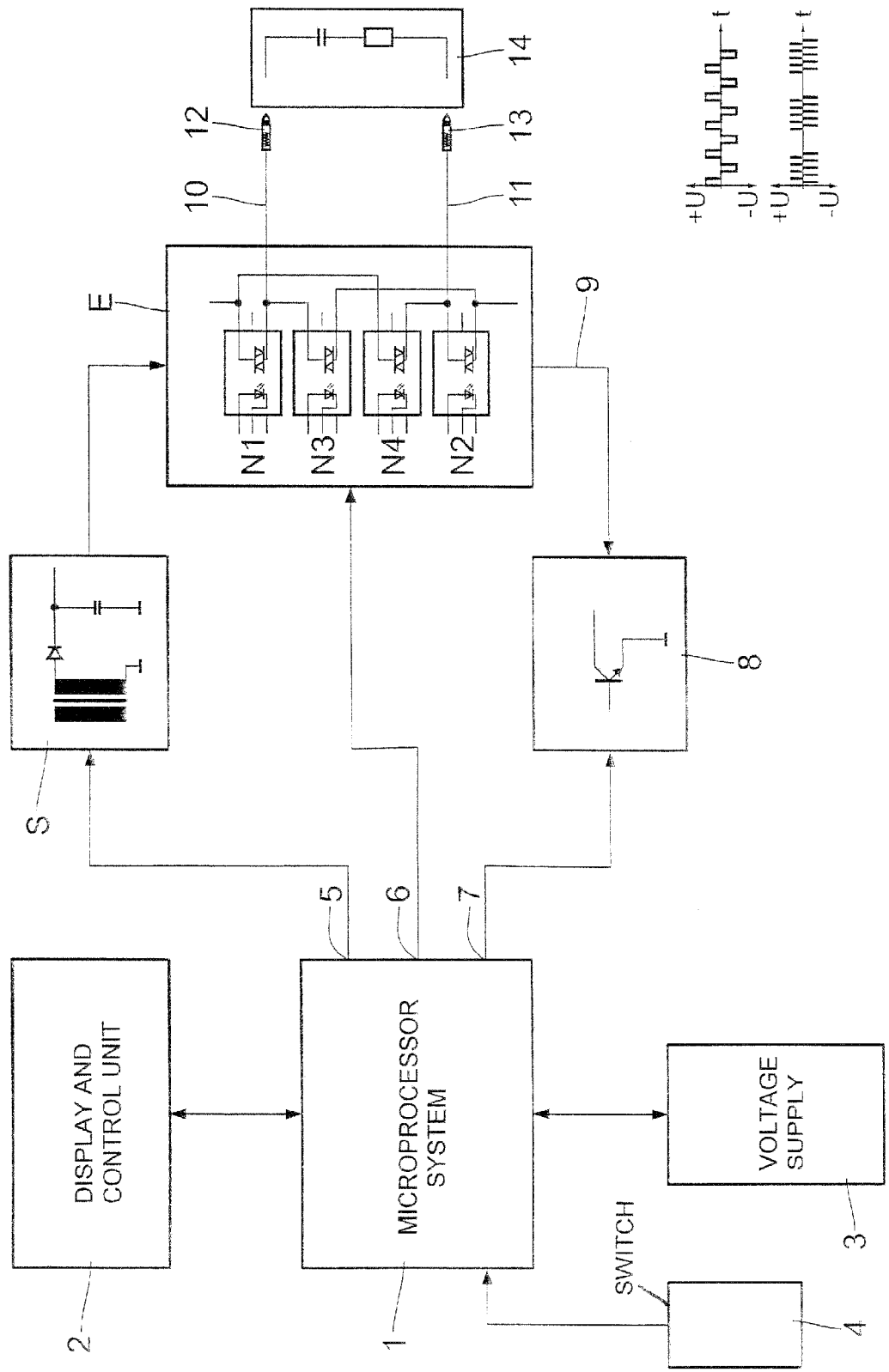
FIG. 1 is a block diagram of an apparatus for electrotherapy according to the invention.

The circuit arrangement seen in FIG. 1 comprises a microprocessor system 1 which is connected to a display and control unit 2, voltage supply 3 and foot-actuated switch 4.

Via a voltage transformer S, a first output 5 of the microprocessor system 1 is connected to a pole reversal and discharge circuit E according to the invention, a second output 6 is directly connected to the circuit E; and a third output 7 is connected to a controllable stabilized power supply 8 which an output 9 of the pole reversal and discharge circuit E applies to.

Via contacts 12 and 13, the outputs 10 and 11 are connected to a patient or, in the block diagram, to a patient-equivalent circuit 14.

FIG. 1, bottom right, illustrates pulses of modifiable phase and frequency at the outputs 10 and 11, the base pulses being plotted at the top and the so-called bursts below.

The pole reversal and discharge circuit E comprises four circuit elements N1 to N4, each having a thyristor triggered by an optocoupler.

Figure 2:
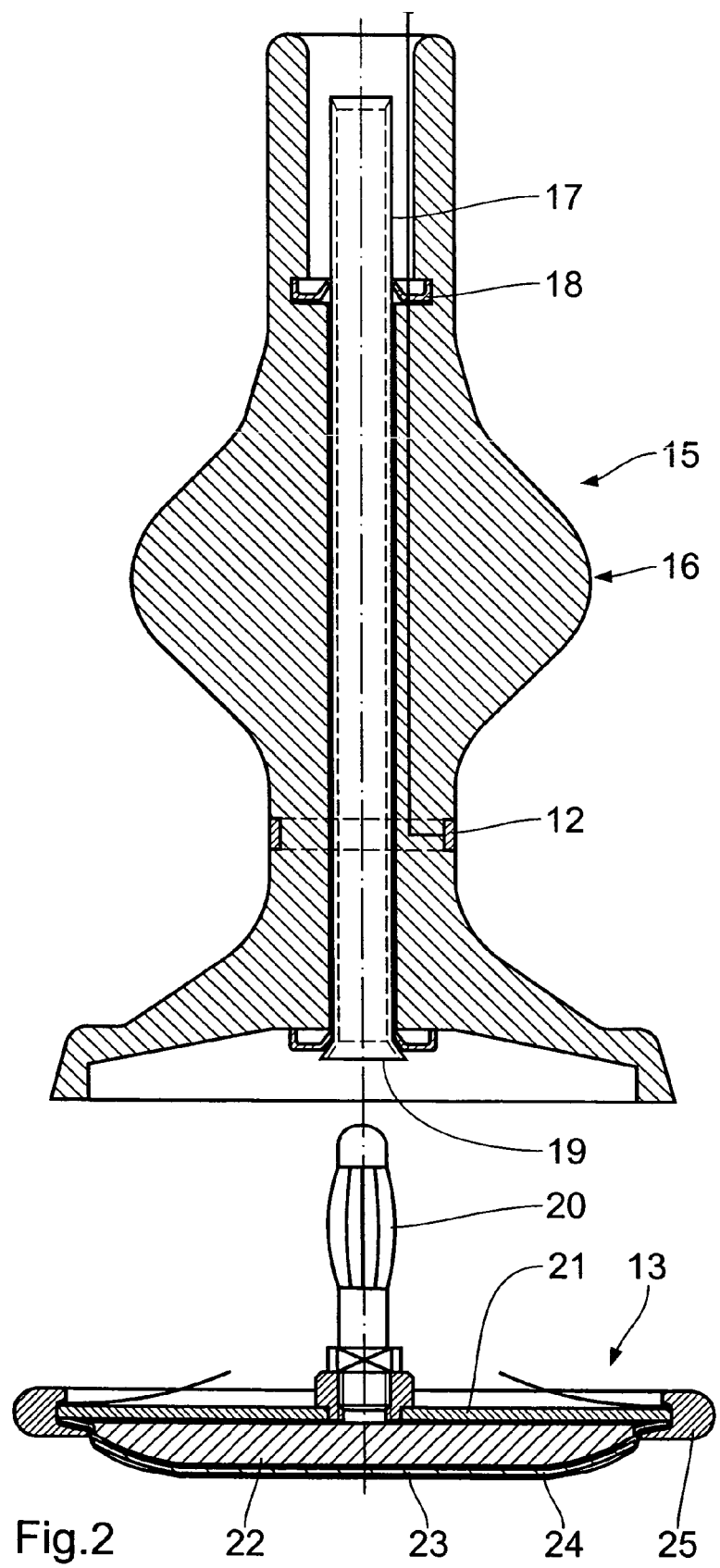
FIG. 2 is a longitudinal sectional view of an electrode arrangement according to the invention.

FIG. 2 illustrates an electrode 15 according to the invention. It comprises a silicone handle 16 of ergonomic shape, in which is disposed a contact sleeve 17 that is fixed by a circlip 18. The contact sleeve 17 is connectable to outputs or contacts 12, 13 of the circuit arrangement of FIG. 1, which is not seen in the drawing.

Insertable into the open bottom end 19 of the contact sleeve 17 is a spring-basket-type plug 20 which is again connected to a metal electrode plate 21, the electrode plate 21 in this way being fixable to the bottom end of the silicone handle 16.

Underneath the electrode plate 21, provision is made for an electrically conductive foam layer 22, underneath which a hydrogel disk 23 is provided, with a vinyl film 24 being stretched over the entire arrangement and secured by a clamping ring 25.

What is claimed is:

1. An apparatus for electrotherapy, comprising a circuit arrangement with a terminal for generation of a sequence of voltage pulses; and two electrodes for application of these voltage pulses to a part of the body that is to be treated; one of the two electrodes having a surface of comparatively high transition resistance and the other electrode having comparatively low transition resistance towards human skin; the electrode with the surface of high transition resistance being movable over the treated part of the body and the surface being a plastic film; with pulse sequences of voltages in a range from 1 to 600 V being generated and a current in a microampere range being produced in human tissue; wherein the pulse sequences have a base frequency of 5 to 250 Hz superimposed by a frequency of 1 to 30 Hz; and wherein said apparatus further comprises a rapid-discharge circuit (E) that includes several thyristors (N1 to N4) that are triggered by optocouplers.

2. An apparatus according to claim 1, wherein an electrode arrangement is provided, comprising the electrode of comparatively high transition resistance and a metal electrode of low transition resistance.

3. An apparatus according to claim 2, wherein the electrode arrangement comprises a handle into which releasably to insert the electrode of comparatively high transition resistance.

4. An apparatus according to claim 3, wherein a spring-basket-type plug is mounted on the electrode of comparatively high transition resistance, the spring-basket-type plug being insertable into a corresponding sleeve on the handle of the electrode arrangement.

5. An apparatus according to claim 2, wherein the metal electrode is covered mechanically or switched off electrically.

6. An apparatus according to claim 1, wherein a foot-actuated switch (4) is provided for switch-over of working parameters.

7. An apparatus according to claim 6, wherein the working parameters are at least one of frequencies and amplitudes.

8. An apparatus according to claim 1, wherein the electrode of comparatively high transition resistance comprises a metal electrode plate with a conductive foam layer provided thereon that is covered by a plastic film, a hydrogel disk being inserted between the foam layer and the plastic film.

9. An apparatus according to claim 8, wherein said plastic film is a vinyl film.

10. An apparatus according to claim 1, wherein the base frequency is approximately 100 Hz.

11. An apparatus according to claim 10, wherein the superimposed frequency is 1 to 10 Hz.

12. An apparatus according to claim 1, wherein the terminal produces continuous or randomized frequency bands.

* * * * *